United States Patent [19]

Dawson et al.

[11] Patent Number: 5,425,867
[45] Date of Patent: Jun. 20, 1995

[54] METHOD AND APPARATUS FOR PRODUCING ELECTROCHEMICAL IMPEDANCE SPECTRA

[75] Inventors: John L. Dawson; David A. Eden; Richard N. Carr, all of Manchester, United Kingdom

[73] Assignee: Capcis March Limited, Manchester, United Kingdom

[21] Appl. No.: 119,192
[22] PCT Filed: Mar. 23, 1992
[86] PCT No.: PCT/GB92/00527
 § 371 Date: Nov. 12, 1993
 § 102(e) Date: Nov. 12, 1993
[87] PCT Pub. No.: WO92/16825
 PCT Pub. Date: Oct. 1, 1992

[30] Foreign Application Priority Data

Mar. 23, 1991 [GB] United Kingdom ............... 9106218

[51] Int. Cl.⁶ ........................................... G01N 27/26
[52] U.S. Cl. ............................... 204/400; 204/404; 204/406; 204/412; 204/434; 324/71.1; 324/71.2; 324/347; 324/348
[58] Field of Search ............... 204/400, 404, 406, 412, 204/434, 153.1, 153.11; 324/425, 71.1, 71.2, 347, 348

[56] References Cited

U.S. PATENT DOCUMENTS

| | | | |
|---|---|---|---|
| 4,575,678 | 3/1986 | Hladky | 204/404 |
| 4,631,116 | 12/1986 | Ludwig | 204/153.1 |
| 5,139,627 | 8/1992 | Eden et al. | 204/404 |

FOREIGN PATENT DOCUMENTS 0084404 7/1983 European Pat. Off. .
0302073 2/1989 European Pat. Off. .
8707022 11/1986 WIPO .

OTHER PUBLICATIONS

Walter, G. W., "A Review of Impedance Plot Method used for Corrosion Performance Analysis of Painted Metals", Corrosion Science, vol. 26, No. 9, pp. 681–703, 1986. No month presently available.

Keddam, Michel., "Reaction Model for Iron Dissolution Studied by Electrode Impedance", J. Electrochem Soc. Electrochemical Science and Technology, pp. 257–267, Feb. 1981.

Anderson, N., "On the Calculation of Filter Coefficients for Maximum Entropy Spectral Analysis", Geophys, vol. 29, pp. 69–72, Feb. 1974.

*Primary Examiner*—John Niebling
*Assistant Examiner*—Bruce F. Bell
*Attorney, Agent, or Firm*—Spensley Horn Jubas & Lubitz

[57] ABSTRACT

A method for producing electrochemical impedance spectra. Spontaneously occuring coupling current noise between an array of electrodes which may be of substantially the same material is detected. A time domain record of the detected current noise is stored and the time domain record of the detected current noise is transformed to the frequency domain. Spontaneously occurring potential noise between the array of electrodes and a further electrode is detected. A time domain record of the detected potential noise is stored and the time domain record of the detected potential noise is transformed to the frequency domain. The frequency domain current noise and potential noise transformations are then transformed to the impedance domain to produce the required electrochemical impedance spectra.

4 Claims, 10 Drawing Sheets

METHOD AND APPARATUS FOR PRODUCING ELECTROCHEMICAL IMPEDANCE SPECTRA

The present invention relates to a method and apparatus for producing electrochemical impedance spectra.

It is well known that useful information concerning electrochemical processes can be obtained from impedance data. Typically an electrochemical impedance spectra is obtained from a system under investigation using perturbative techniques. For example a sine wave, pulse or random noise signal is applied to an electrochemical cell under investigation and the cell response is correlated with the applied signal. The resultant data is typically presented as either a Bode plot, a frequency spectra of impedance and phase angle against frequency, or a Nyquist diagram of real impedance (resistive) and complex impedance (capacitive) with frequency as a parameter. The article "A Review of Impedance Plot Methods used for Corrosion Performance Analysis of Painted Metals" by G. W. Walter, *Corrosion Science*, Vol 26, No. 9 PP681–703, 1986 describes Bode and Nyquist plots in some detail. There are however a number of earlier publications presenting similar information, see for example "Electrochemical Impedance of Pure Iron at various Potentials in Sulphuric Acid", (M. Keddam, O. R. Mattos and H. Takenouti, *J. Electrochem. Soc.* 128, 257 (1981)).

The interpretation of electrochemical impedance spectra is a subject of continuing scientific debate. Nevertheless, it is generally agreed that information on electron transfer processes, diffusion, absorbed species and electro-crystallization can be obtained from analysis of the loops that appear on the Nyquist-type impedance diagrams. These loops, sometimes referred to as relaxations, may be either of capacitive or of inductive type (negative capacitance) and, depending on the electrochemical process or reactions involved, each loop can be ascribed to the presence of an adsorbed species or a reaction rate constant. The reaction rate constant may also involve consideration of the surface coverage and/or surface concentration of an electroactive species.

The use of the known perturbative techniques to generate electrochemical impedance spectra can provide useful information and as a consequence such techniques have become widely accepted. It is the case however that the application of the perturbation signal may itself produce impedance spectra which are a function of the perturbation signal itself, for example due to the electrode shape and cell configuration. Furthermore, at low frequencies the time taken for the measurement from which the spectra is derived can lead to errors in the data due to spontaneous changes which occur naturally within the system being studied.

It is known to monitor the corrosion of metal components by reference to spontaneously generated fluctuations in the potential of an electrode. In one known system, as described in European Patent Specification EP 0084404, the electrochemical potential of an electrode is monitored and the monitored signal is filtered to remove DC and higher frequency AC components. This provides a measure of the rate of corrosion of the electrode.

It is also known from European Patent Specification EP 0302073 to measure electrochemical current noise originating in an electrode array and to compare the electrochemical current noise with a coupling current between two electrodes of the array to generate an output which is indicative of the degree to which corrosion is localised. In addition, electrochemical current noise and electrochemical potential noise are compared to provide an output which is indicative of the overall rate of corrosion. This output does not however present the detailed information available from electrochemical impedance spectra.

It is an object of the present invention to obtain electrochemical impedance spectra from an electrochemical system without it being necessary to apply a perturbing signal to the system. It has surprisingly been found that such spectra can be generated from spontaneously occurring noise.

According to the present invention, there is provided a method for producing electrochemical impedance spectra, wherein spontaneously occurring coupling current noise between at least two electrodes is detected, a time domain record of the detected current noise is stored, the time domain record of the detected current noise is transformed to the frequency domain, spontaneously occurring potential noise between at least one of said electrodes and a further electrode is detected, a time domain record of the detected potential noise is stored, the time domain record of the detected potential noise is transformed to the frequency domain, and the frequency domain current noise and potential noise transformations are combined to produce an impedance domain transform.

Preferably, the coupling current noise is detected between two electrodes of substantially the same material.

The time domain to frequency domain transformations may be effected using conventional techniques, e.g. the maximum entropy method or specific versions of the Fast Fourier Transform. The frequency domain to impedance domain transformation may be effected for example by deriving the magnitude of the impedance at a predetermined frequency from the quotient of the amplitude of the potential at that frequency and the amplitude of the coupling current at that frequency. Alternatively, the frequency to impedance domain transformation may be effected by deriving phase information from the difference of the phase of the potential and the phase of the current.

The present invention also provides an apparatus for producing electrochemical impedance spectra, comprising an array of at least two electrodes, means for detecting spontaneously occurring coupling current noise between the or at least two of the array of electrodes, means for storing a time domain record of the detected current noise, means for transforming the time domain record of the detected current noise to the frequency domain, a further electrode, means for detecting spontaneously occurring potential noise between said further electrode and at least one of said at least two electrodes, means for storing a time domain record of the detected potential noise, means for transforming the time domain record of the detected potential noise to the frequency domain, and means for combining the frequency domain current noise and potential noise transformations to produce an impedance domain transform.

Preferably, the electrodes of said array are of substantially the same material.

Preferably, a zero resistance ammeter is connected between electrodes of said array to provide a measure of the coupling current, a filter is connected to the ammeter to remove DC and AC components of the measured current having a frequency greater than a predetermined threshold frequency, a high impedance buffer is connected between said array and said further electrode to provide a measure of the potential noise, a filter is connected to the buffer to remove DC and AC components of the detected potential having a frequency greater than a predetermined threshold frequency.

The said further electrode may preferably be fabricated from a substantially non-corrodible material.

In one embodiment of the invention a surface covered by a coating may form a first electrode of the array and a second electrode of the array may be formed by a polarisable substantially non-corrodible material, the second said electrode being positioned on the outside of the coating.

Figure 1:
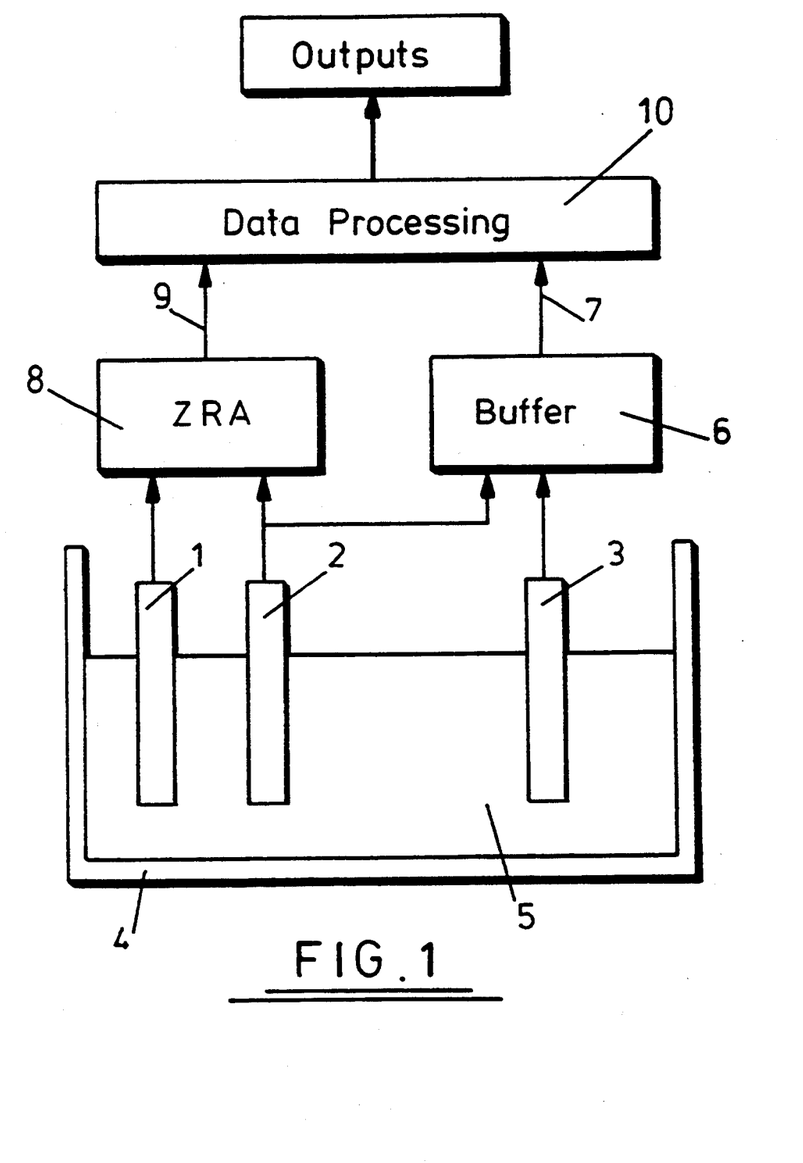
FIG. 1 is a schematic illustration of an apparatus in accordance with the present invention.
Figure 2:
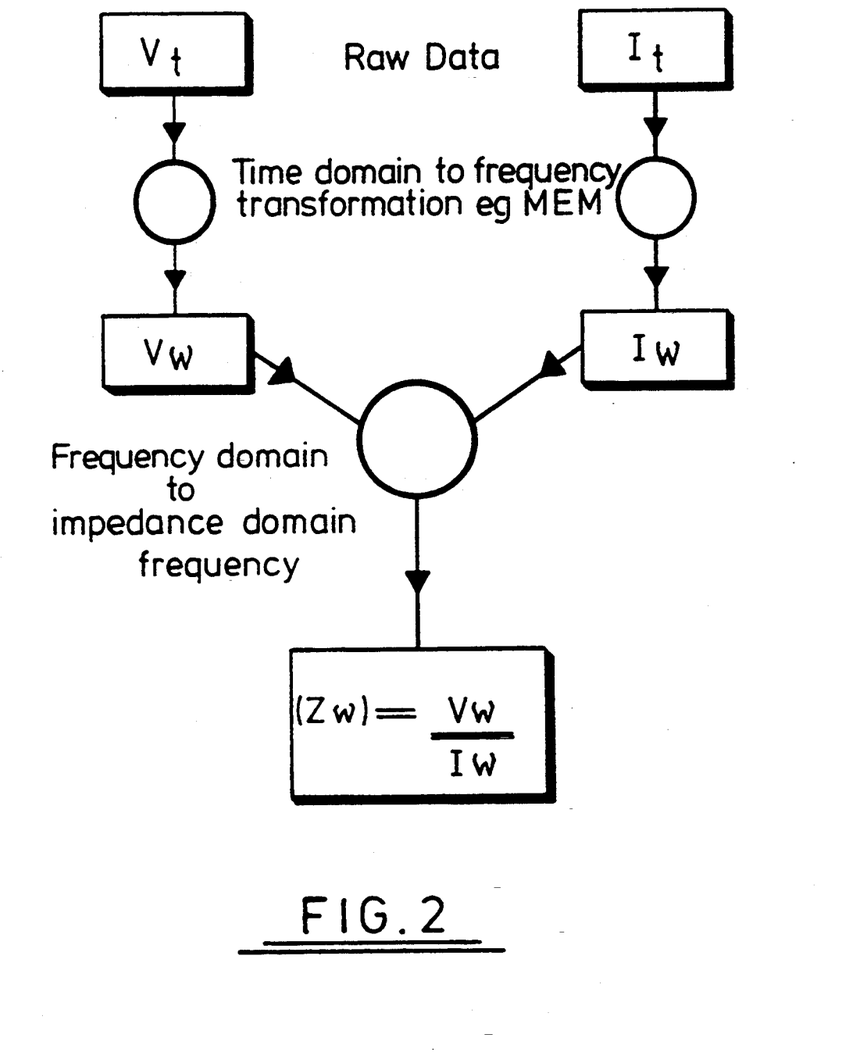
FIG. 2 is a flow diagram illustrating the operation of the embodiment of FIG. 1.

Referring to FIG. 1, the illustrated system comprises three electrodes, 1, 2 and 3 suspended within a container 4 and immersed in a liquid 5 within the container. The electrodes 1 and 2 are substantially identical in shape and composition such that electrochemical noise can be expected as a result of an electrochemical reaction between the electrodes 1 and 2 and the liquid 5. In contrast, the electrode 3 is a reference electrode or may be of an inert metal or material to provide a pseudo-reference or even of the same composition as electrodes 1 and 2.

The electrode 3 is connected to a high impedance buffer 6 which also receives an input from the electrode 2 and provides an output 7 representative of the spontaneously generated electrochemical potential noise between the electrodes 2 and 3. That potential is referred to herein as $V_t$.

The electrodes 1 and 2 are connected to a zero resistance ammeter 8 which produces an output 9 corresponding to the spontaneously generated coupling current noise between the electrodes 1 and 2. That coupling current noise is referred to herein $I_t$.

The spontaneous current and potential noise that is monitored is produced by transient electrochemical events. The existence of this noise phenomena is well known and often referred to as 1/f or low frequency noise and appears to be the result of stochastic processes, electrochemical kinetic transients, and in some cases diffusion processes.

The signals 7 and 9 are representative of the instantaneous potential and current noise signals derived from the electrode array. These signals are delivered to a data processing unit 10 which stores a time record of the two input signals and transforms the two signals into the frequency domain using the maximum entropy method. This method is described for example in the article "On the Calculation of Filter Coefficients for Maximum Entropy Spectral Analysis", Anderson, *Geophys*, Vol. 39, PP69–72, February 1974. Thus as a result of this transformation two separate pieces of information are derived, namely the frequency spectrum of the current noise and the frequency spectrum of the potential noise in terms of both amplitude and phase.

Figure 3:
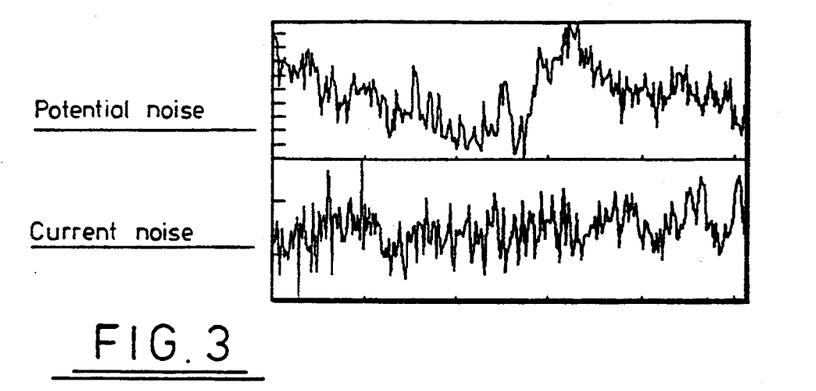
FIGS. 3, 4 and 5 respectively illustrate noise signals, frequency spectra and impedance spectra derived from the apparatus described with reference to FIGS. 1 and 2.
Figure 4:
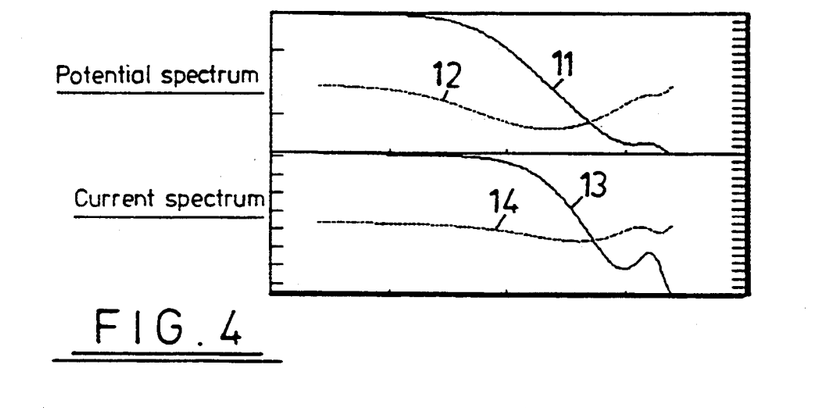

The upper half of FIG. 3 shows a time record of potential noise in one example and the lower half of FIG. 3 shows a time record of the current noise for the same example. The upper half of FIG. 4 shows the frequency spectra for the potential noise of FIG. 3, curve 11 representing the amplitude and curve 12 representing the phase angle. The lower half of FIG. 4 represents the frequency spectrum for the current noise of FIG. 3, curve 13 representing amplitude and curve 14 representing phase angle. In the curves of FIG. 4, frequency increases from left to right.

Referring again to FIG. 1, after conversion from the time to frequency domains in the data processor 10, the data processor then performs a further transformation to transform the frequency domain data into the impedance domain. This is achieved by manipulating the current and potential noise data to provide the impedance by the transform:

$$|Z_w| = V_w/I_w$$

where $Z_w$ is the magnitude of the impedance at frequency w, $V_w$ is the amplitude of the potential at frequency w, and $I_w$ is the amplitude of the current at frequency w. This information may then be presented in the form of a Bode diagram, that is log Zw versus log (frequency). In a similar manner, the phase information of the signals may be obtained by simple subtraction:

$$\text{Phase } (Z) = \text{Phase } (V) - \text{Phase } (I).$$

This data may then be further processed to provide a Nyquist diagram in which the real part of the impedance is plotted against the imaginary part of the impedance with frequency as a parameter.

Figure 5:
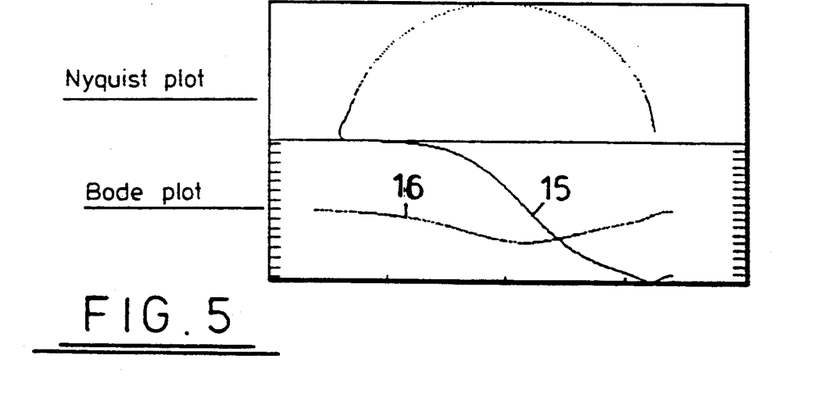

The upper half of FIG. 5 represents a Nyquist plot derived from the information in FIG. 4. The lower part of FIG. 5 is a Bode diagram representing the information in FIG. 4, curve 15 representing the electrochemical combination of the two amplitudes and curve 16 representing the combination of the two phase angles. In accordance with the usual electrochemical conventions, the frequency increases from right to left in the upper half of FIG. 5 and from left to right in the lower half of FIG. 5.

The potential and current noise signals represented in FIG. 3 contain low frequency impedance information, typically in the frequency range of 0.5 mHz to 1 Hz. This low frequency data provides information relating to the spontaneous electrochemical processes occurring in the system under investigation. It is the spontaneous processes that are of interest. Thus in contrast to the known perturbative techniques outlined above, in which the system is deliberately disturbed to generate a response, the low frequency impedance data that is processed in the described embodiment of the invention is generated exclusively by the electrochemical processes under investigation.

The low frequency impedance data enables information to be obtained relating to charge transfer processes and to complex reaction kinetics involving adsorbed intermediates and complex parallel processes. Thus in the case of corrosion of metals for example, the information obtained may relate to the degree of localised corrosion attack, pitting, stress corrosion cracking and general corrosion. In the case of other types of electrochemical activity, for example on electrodes in electrochemical conversion systems, fuel cells and batteries, electroless plating, coated electrodes, polymer modified electrodes, doped electrodes, electroactive catalytic surfaces, photochemical electrodes, bioelectrodes or biosensors and other electrochemical detectors or sensors as used for monitoring and control purposes, the information obtained may relate to exchange current densities, species concentration and surface state. The measurements so obtained would include information on processes such as electron transfer, exchange currents, reaction rate constants, concentrations and surface excess and interfacial fluxes.

Thus the present invention is applicable to the study of electrochemical processes in general, not just corrosion processes.

The present invention is concerned with the derivation of data for interpretation rather than interpretation of that data itself. The above mentioned article by G. W. Walter includes a general discussion of the analysis of Bode and Nyquist plots to derive information relating to electrochemical processes. It will however be appreciated that it is possible to derive information from impedance relating to electrochemical processes as described above and in particular obtain information about low frequency processes such as capacitance values, charge transfer resistance values, polarisation resistance values, the presence of multiple time constant processes, and the presence of adsorption effects as well as exchange current densities and corrosion currents.

Figure 6:
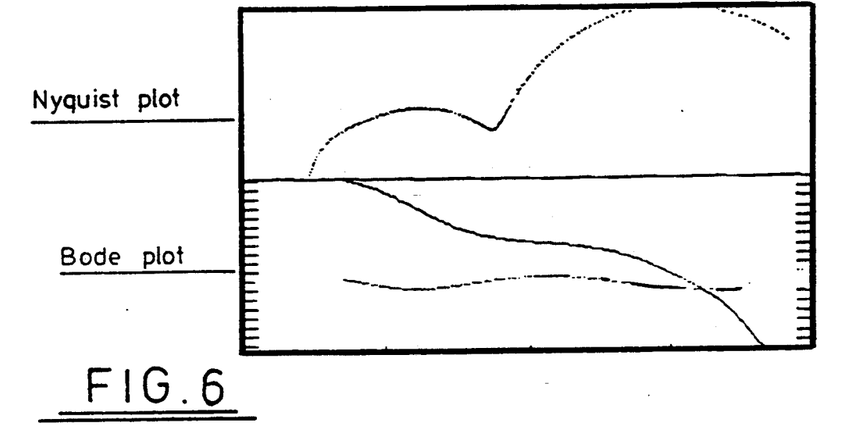
FIGS. 6, 7, 8, 9, 10 and 11 illustrate further impedance spectra related respectively to copper immersed in drinking water, Muntz metal immersed in cooling water, steel reinforcement corroding in concrete, passive steel reinforcement in concrete, a steel specimen coated with an organic paint and a quihydrone redox in an acidic solution.
Figure 7:
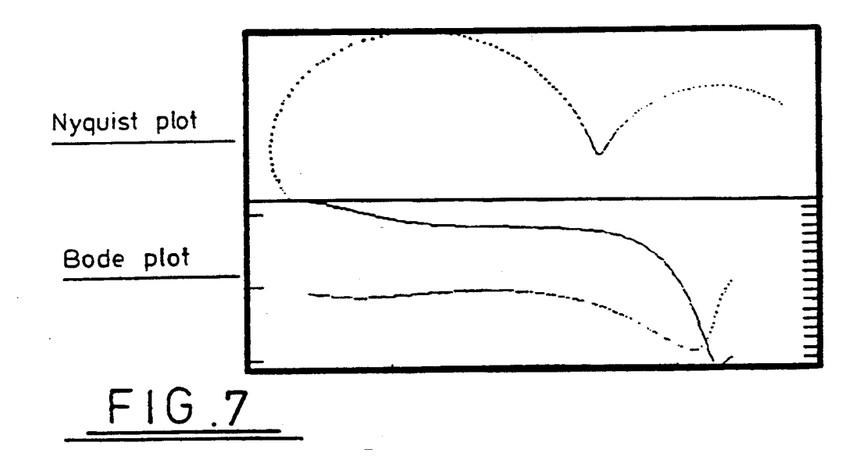

By way of further example, FIGS. 6, 7, 8, 9, 10 and 11 show further Nyquist and Bode plots, the information being represented in these figures in exactly the same manner as in the case of FIG. 5. It will be noted that there are dramatic differences between the various plots and from these differences significant information about electrochemical processes can be derived. FIG. 6 represents data obtained from pure copper immersed in drinking water, and FIG. 7 represents data obtained from Muntz metal (60/40 brass) immersed in cooling water.

Figure 8:
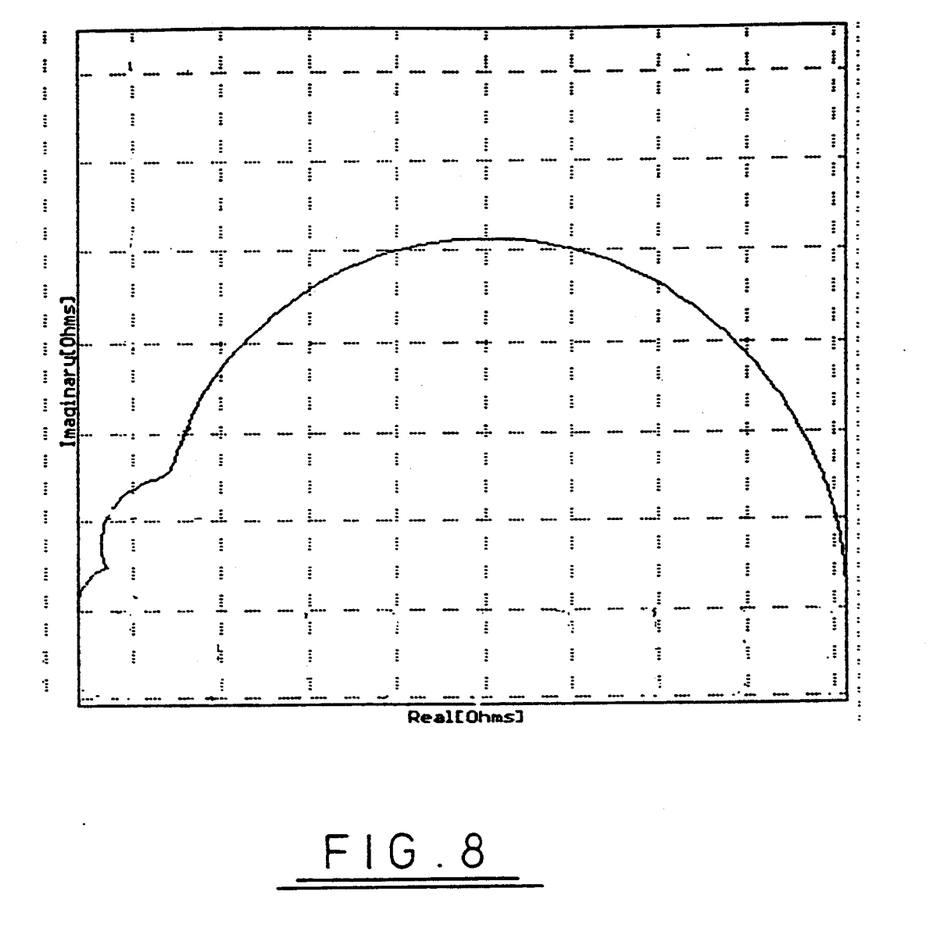
Figure 9:
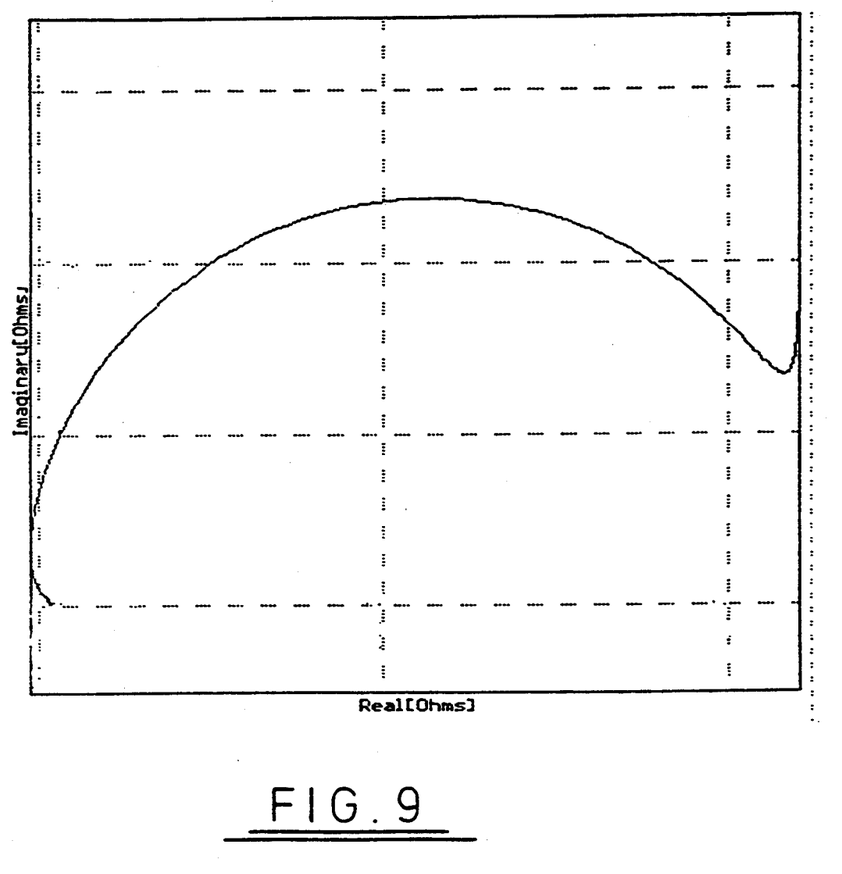

FIG. 8 illustrates the impedance derived from a steel reinforcement bar actively corroding in concrete. The plot indicates three time constants and a low resistance to corrosion. In contrast, FIG. 9 illustrates the impedance derived from a passive, essentially non-corroding, steel reinforcement bar in concrete. In comparison to FIG. 8, this plot shows a higher resistance to corrosion and low frequency diffusion controlled processes.

Figure 10:
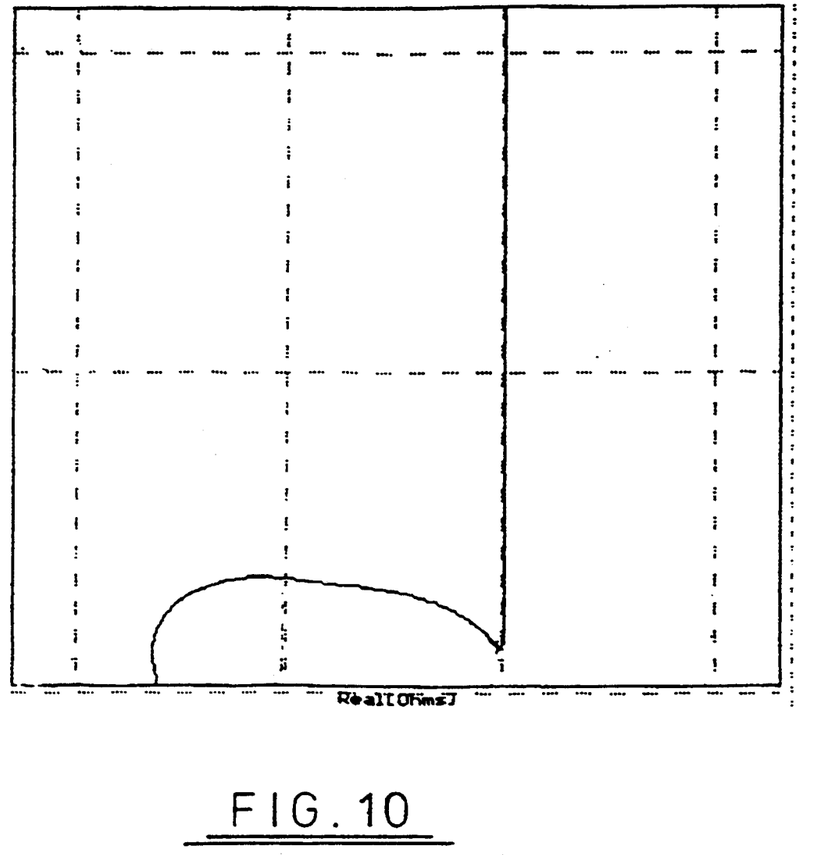

The invention may be used for detecting the impedance of a metallic surface covered by a coating such as an organic paint, anodised aluminium or a concrete cover. The coupling current noise is measured between the metal surface to be evaluated and a substantially non-corrodible electrode positioned on the outside of the coating or cover via the zero resistance ammeter 8. The further electrode used to measure the potential noise should preferably be fabricated from a non-corrodible material. FIG. 10 illustrates the impedance response obtained from a quality primer coat applied to a mild steel sample. This is an example of monitoring high impedance protection systems.

Figure 11:
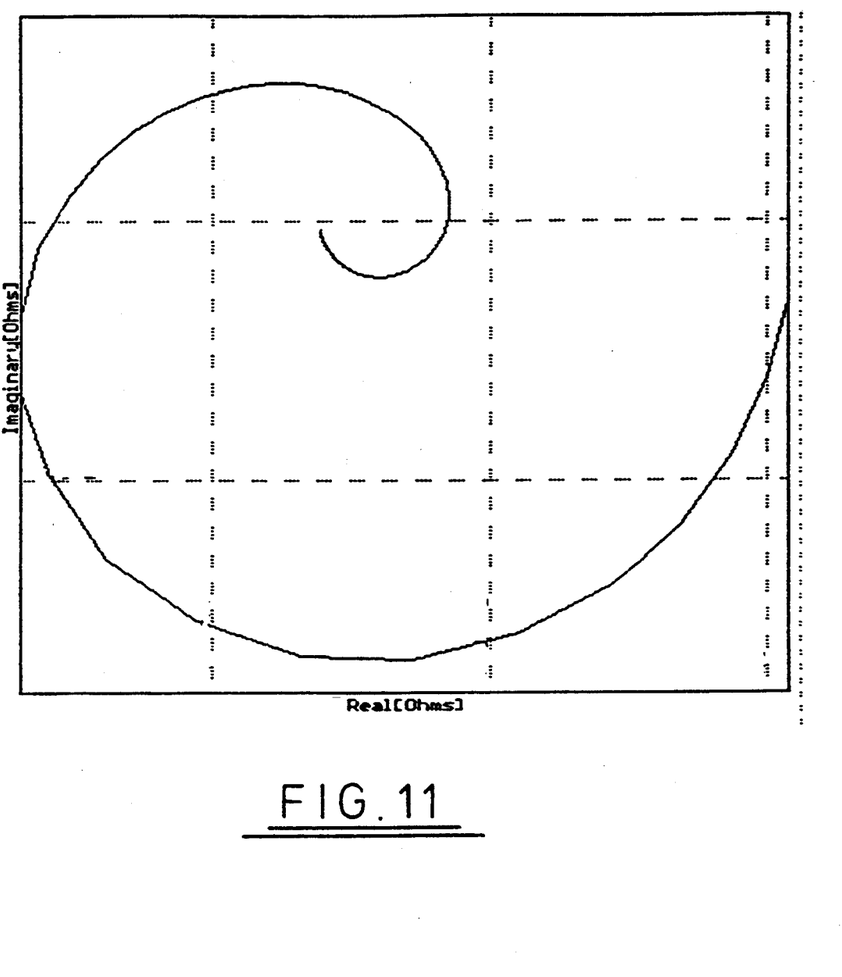

The method may also be used to detect the electrochemical impedance of a redox electrode system in which an array of electrodes is fabricated from an essentially non-corrodible material and is exposed to an electrolyte containing either an inorganic or organic redox system. FIG. 11 illustrates a typical redox response obtained from inert electrodes in an acidic quihydrone redox system. The plot shows a complex adsorption and change transfer process.

The method can be used for detecting the electrochemical impedance of electrodes comprising an electrochemical power conversion system. In this case the electrodes are defined by the electrodes or plates of a battery or fuel cell system for instance.

The method may be used for detecting the electrochemical impedance of electrochemically active biosensors or biological systems. In this case an array of electrodes fabricated from an essentially non-corrodible but electrochemically active material is exposed in an in-vivo or in-vitro electrolyte containing biological agents, compounds or species of interest.

Figure 12:
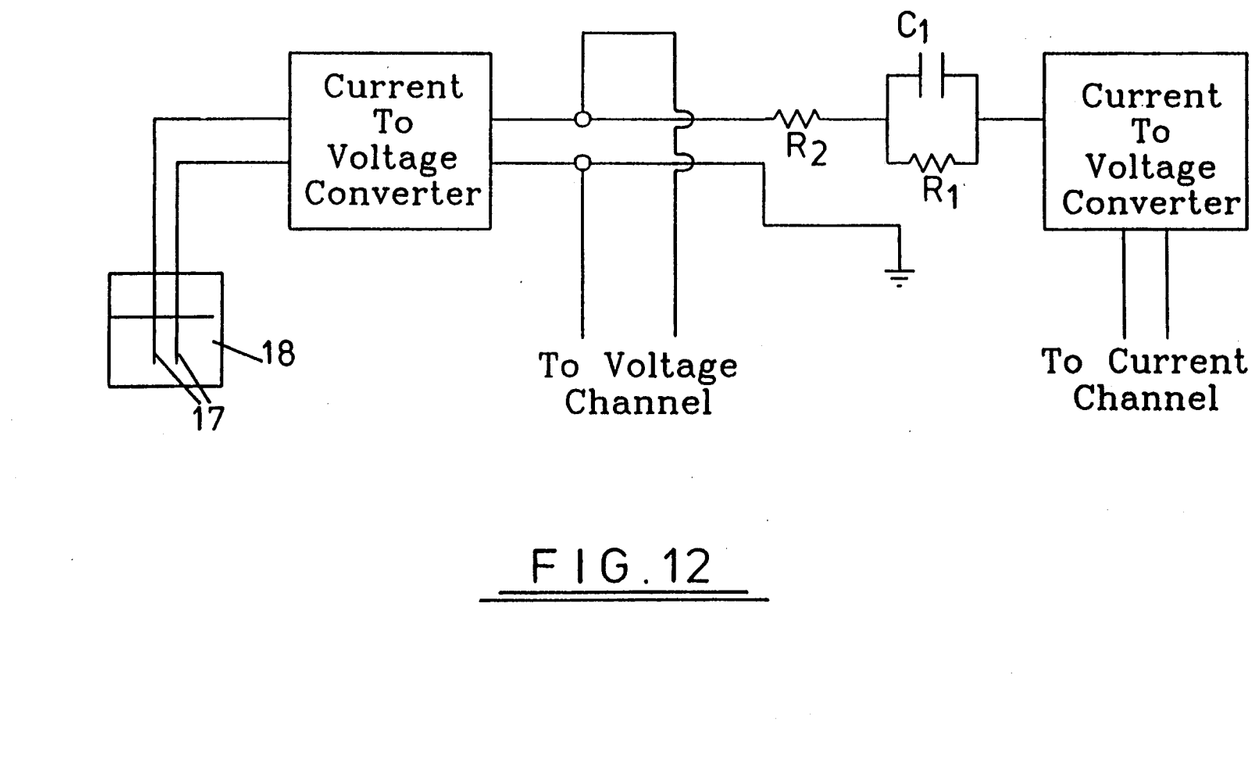
FIG. 12 illustrates a demonstration circuit used to test the accuracy of the invention.
Figure 13:
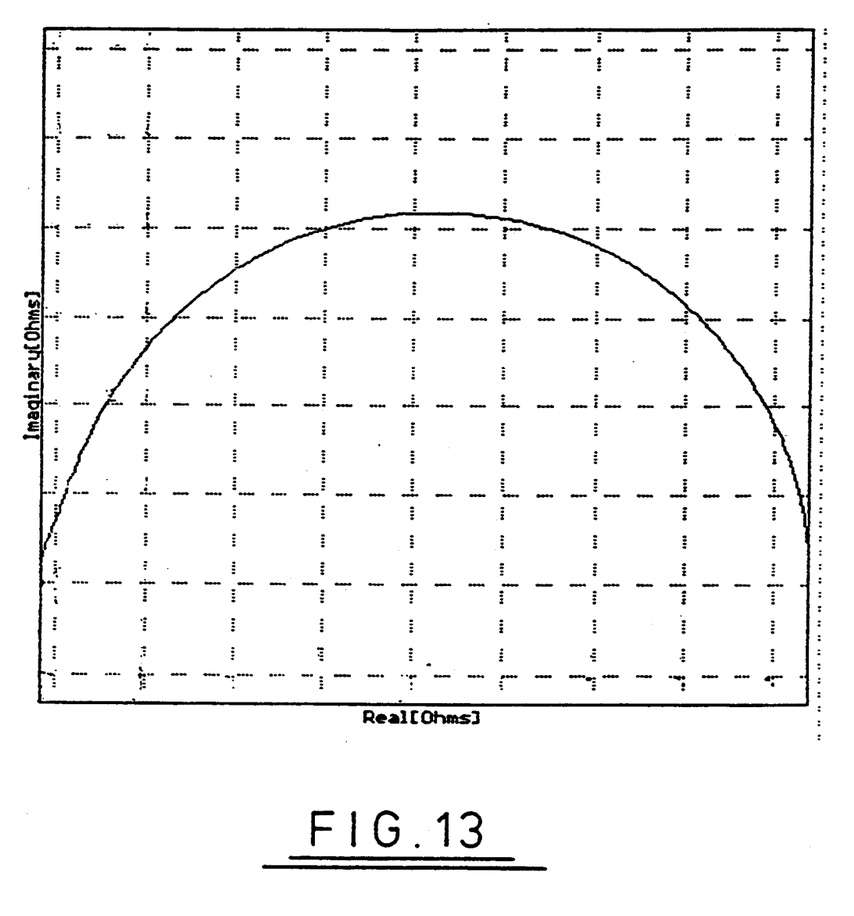
FIG. 13 illustrates impedance spectra obtained from the demonstration circuit.

FIG. 12 illustrates a demonstration circuit used to verify that the abovedescribed transformation method is able to produce electrochemical impedance from the time domain current and potential signals. An equivalent circuit and an externally imposed low frequency voltage noise source are used to obtain the impedance data. Such circuitry is conventionally used as a means for measuring electrochemical impedance from spectroanalysis, but here is used to demonstrate the accuracy of the data transformation processes of the present invention. The equivalent circuit comprises a parallel resistor $R_1$ and capacitor $C_1$ combination in series with a resistor $R_2$. Resistor $R_1$ has a value of 1M $\Omega$, resistor $R_2$ has a value of 10K $\Omega$, and capacitor $C_1$ has a value of 10 $\mu F$. This circuit essentially models a typical simple electrochemical interface. A corroding system of mild steel electrodes 17 in salt water 18 provides the noise signal necessary for the perturbation of the circuit. The random noise signal emanating from the corroding steel electrodes 17 is supplied to the equivalent circuit and the resulting current and voltage response is measured and analyzed to determine the magnitude of the two resistors and capacitor from Bode and Nyquist plots. FIG. 13 shows the results of one such experiment. The experimentally obtained data gave resistance and capacitor values within 10% of the actual values quoted above.

We claim:

1. An apparatus for producing impedance spectra, comprising an array of at least two electrodes, means for detecting spontaneously occurring coupling current noise between the or at least two of the array of electrodes, means for storing a time domain record of the detected current noise, means for transforming the time domain record of the detected current noise to the frequency domain, a further electrode, means for detecting spontaneously occurring noise between said further electrode and said at least two electrodes, means for storing a time domain record of the detected potential noise, means for transforming the time domain record of the detected potential noise to the frequency domain, and means for transforming the frequency domain current noise and potential noise transformation to the impedance domain, wherein a surface covered by a coating forms a first electrode of the array, a second electrode of the array is formed by a polarisable substantially non-corrodible material, the second said electrode being positioned on the outside of the coating.

2. An apparatus for producing impedance spectra, comprising an array of at least two electrodes, means for detecting spontaneously occurring coupling current noise between the at least two of the array of electrodes, means for storing a time domain record of the detected current noise, means for transforming the time domain record of the detected current noise to the frequency domain, a further electrode, means for detecting spontaneously occurring noise between said further electrode and said at least two electrodes, means for storing a time domain record of the detected potential noise, means for transforming the time domain record of the detected potential noise to the frequency domain, and means for transforming the frequency domain current noise and potential noise transformation to the impedance domain, wherein the said further electrode is fabricated from a substantially non-corrodible material.

3. An apparatus according to claim 1 or 2, wherein the electrodes of said array are of substantially the same material.

4. An apparatus according to claim 1 or 2, wherein a zero resistance ammeter is connected between electrodes of said array to provide a measure of the coupling current, a filter is connected to the ammeter to remove DC and AC components of the measured current having a frequency greater than a set threshold frequency, a high impedance buffer is connected between said array and said further electrode to provide a measure of the potential noise, a filter is connected to the buffer to remove DC and AC components of the detected potential having a frequency greater than a set threshold frequency.

* * * * *